US00PP14507P29

(12) United States Plant Patent
Sakazaki

(10) Patent No.: US PP14,507 P2
(45) Date of Patent: Feb. 3, 2004

(54) SUTERA PLANT NAMED 'GICOMWHI-14'

(50) Latin Name: *Sutera cordata*
Varietal Denomination: Gicomwhi-14

(75) Inventor: Ushio Sakazaki, Shiga Prefecture (JP)

(73) Assignee: Plant 21 LLC, San Marco, CA (US)

( * ) Notice: Subject to any disclaimer, the term of this patent is extended or adjusted under 35 U.S.C. 154(b) by 0 days.

(21) Appl. No.: 10/385,243

(22) Filed: Mar. 10, 2003

(51) Int. Cl.[7] ..... A01H 5/00
(52) U.S. Cl. ..... Plt./263
(58) Field of Search ..... Plt./263

(56) References Cited

U.S. PATENT DOCUMENTS

PP10,966 P * 6/1999 Rother ..... Plt./263
PP12,026 P2 * 7/2001 Theobald ..... Plt./263
PP12,682 P2 * 6/2002 Polman ..... Plt./263
PP12,689 P2 * 6/2002 Churchus ..... Plt./263
2003/0115651 P1 * 6/2003 Brandkamp ..... Plt./263
2003/0131388 P1 * 7/2003 Westhoff ..... Plt./263

OTHER PUBLICATIONS

UPOV ROM GTITM Computer Database, GTI Jouve Retrieval Software 2003/02 Citations for 'Gicomwhi14'.*

* cited by examiner

*Primary Examiner*—Bruce R. Campell
*Assistant Examiner*—W C Haas
(74) *Attorney, Agent, or Firm*—C. A. Whealy

(57) ABSTRACT

A new and distinct cultivar of Sutera plant named 'Gicomwhi-14', characterized by its low mounding and trailing plant habit; vigorous growth habit; freely and continuous branching habit; numerous large salverform flowers that are white in color; and good garden performance.

1 Drawing Sheet

Botanical classification/cultivar designation: *Sutera cordata* cultivar Gicomwhi-14.

BACKGROUND OF THE INVENTION

The present Invention relates to a new and distinct cultivar of Sutera plant, botanically known as *Sutera cordata*, and hereinafter referred to by the cultivar name 'Gicomwhi-14'.

The new Sutera is a product of a planned breeding program conducted by the Inventor in Hikone, Shiga Prefecture, Japan. The objective of the breeding program is to create new vigorous Suteras with large and numerous flowers.

The new Sutera originated from a cross-pollination made by the Inventor in April, 1999, of the *Sutera cordata* cultivar Blizzard, disclosed in U.S. Plant Pat. No. 10,966, as the female, or seed parent, with the *Sutera cordata* cultivar Pink Domino, not patented, as the male, or pollen parent. The new Sutera was chosen as a single plant from the resulting progeny of the cross-pollination by the Inventor in July, 2000, in a controlled environment in Gensingen, Germany.

Asexual reproduction of the new cultivar by terminal cuttings taken in Gensingen, Germany since August, 2000, has shown that the unique features of this new Sutera are stable and reproduced true to type in successive generations.

SUMMARY OF THE INVENTION

Plants of the cultivar Gicomwhi-14 have not been observed under all possible environmental conditions. The phenotype may vary somewhat with variations in environment such as temperature and light intensity without, however, any variance in genotype.

The following traits have been repeatedly observed and are determined to be the unique characteristics of 'Gicomwhi-14'. These characteristics in combination distinguish 'Gicomwhi-14' as a new and distinct Sutera cultivar:

1. Low mounding and trailing plant habit.
2. Vigorous growth habit.
3. Freely and continuous branching habit.
4. Numerous large salverform flowers that are white in color.
5. Good garden performance.

Compared to plants of the female parent, the cultivar Blizzard, plants of the new Sutera are more compact and have much larger flowers. Compared to plants of the male parent, the cultivar Pink Domino, plants of the new Sutera have much larger flowers.

Plants of the new Sutera are most similar to plants of the cultivar Giwhisto-12, disclosed in U.S. Plant patent application Ser. No. 10/228,454. In side-by-side comparisons conducted in Gensingen, Germany, plants of the new Sutera were more compact, had lighter green-colored foliage, and had larger flowers.

Plants of the new Sutera can be compared to plants of the Sutera cultivar Cabana, not patented. In side-by-side comparisons conducted in Gensingen, Germany, plants of the new Sutera differed from plants of the cultivar Cabana in the following characteristics:

1. Plants of the new Sutera had a more uniform plant habit than plants of the cultivar Cabana.
2. Plants of the new Sutera had smaller and darker green-colored foliage than plants of the cultivar Cabana.
3. Plants of the new Sutera were more freely flowering than plants of the cultivar Cabana.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which more accurately describe the colors of the new Sutera.

The photograph at the top of the sheet comprises a side perspective view of a typical flowering plant of 'Gicomwhi-14' grown in a 15-cm container.

The photograph at the bottom of the sheet comprises a close-up view of typical flowers, flower buds and leaves of 'Gicomwhi-14'.

DETAILED BOTANICAL DESCRIPTION

The aforementioned photographs and following observations and measurements describe plants grown in Bonsall, Calif., in an outdoor nursery under full sunlight conditions during the winter with day temperatures ranging from 18 to 35° C. and night temperatures ranging from 7 to 18° C. After planting rooted cuttings, plants were grown for about nine weeks in 15-cm containers. Color references are made to The Royal Horticultural Society Colour Chart, 1995 Edition, except where general terms of ordinary dictionary significance are used.

Botanical classification: *Sutera cordata* cultivar Gicomwhi-14.

Parentage:

*Female parent.*—*Sutera cordata* cultivar Blizzard, disclosed in U.S. Plant Pat. No. 10,966.

*Male parent.*—*Sutera cordata* cultivar Pink Domino, not patented.

Propagation:

*Type cutting.*—Terminal vegetative cuttings.

*Time to initiate roots.*—Summer: About 18 days at 22° C. Winter: About 22 days at 22° C.

*Time to produce a rooted cutting.*—Summer: About 24 days at 22° C. Winter: About 30 days at 24° C.

*Root description.*—Fine; white in color.

*Rooting habit.*—Freely branching.

Plant description:

*Form.*—Initially upright, then low mounding and trailing; compact; uniform. Freely branching with about ten lateral branches and numerous secondary lateral branches per plant. Vigorous growth habit.

*Plant height.*—About 8 cm.

*Plant diameter.*—About 56 cm.

*Lateral branches.*—Length: About 30 cm. Diameter: About 3 mm. Internode length: About 2.5 cm. Texture: Pubescent. Color: 145A.

*Foliage description.*—Arrangement: Opposite; simple. Quantity per lateral branch: About 30 to 32. Length: About 2.3 cm. Width: About 2.5 cm. Shape: Roughly ovate. Apex: Acute. Base: Truncate to attenuate. Margin: Serrate. Texture, upper surface: Pubescent; coarse; glandular. Texture, lower surface: Glabrous; coarse; glandular. Venation pattern: Pinnate, arcuate. Fragrance: Grassy. Color: Developing foliage, upper surface: 146B. Developing foliage, lower surface: 146C. Fully expanded foliage, upper surface: 147A. Fully expanded foliage, lower surface: 147B. Venation, upper and lower surfaces: 146C. Petiole length: About 7 mm. Petiole diameter: About 1 mm. Petiole color: 146B.

Flower description:

*Flower type and habit.*—Solitary axillary flowers; salverform; slender corolla tubes flare abruptly into five rounded lobes. Flowers persistent. Very freely flowering; typically two flowers per node and about 28 flower buds and open flowers per lateral branch. Flowers face mostly upward or outward. Flowers persistent.

*Natural flowering season.*—Plants typically flower from spring until fall; flowering continuous during this period.

*Flower longevity on the plant.*—About five to seven days.

*Fragrance.*—None detected.

*Flower size.*—Diameter: About 2 cm. Tube length: About 1.5 cm. Throat diameter, distal end: About 4 mm. Tube diameter, proximal end: About 1.5 mm.

*Flower buds.*—Length: About 1 cm. Diameter: About 4 mm. Shape: Obovate. Color: 157A to 157B.

*Corolla.*—Quantity/arrangement: Five fused petals; slender corolla tube flaring abruptly into five rounded lobes. Petal lobe length from throat: About 8 mm. Petal lobe width: About 7 mm. Petal lobe shape: Roughly spatulate. Petal lobe apex: Rounded. Petal lobe margin: Entire. Texture: Smooth, satiny. Color: When opening, upper surface: 155D. When opening, lower surface: 155B. Fully opened, upper and lower surfaces: More white than 155D. Flower throat (inside): 14A. Flower tube (outside): Towards apex, more white than 155D; towards base, close to 151B.

*Sepals.*—Arrangement/appearance: Single whorl of five sepals fused at base; shallow cup-shaped calyx. Length: About 8 mm. Width: About 1 mm. Shape: Narrow, linear. Apex: Acuminate. Margin: Entire. Texture, upper and lower surfaces: Slightly pubescent. Color, upper and lower surfaces: 146A.

*Peduncles.*—Length: About 8 mm. Width: About 1 mm. Angle: About 30 to 45° from the stem. Strength: Strong; slender. Texture: Smooth. Color: 144B.

*Reproductive organs.*—Stamens: Quantity per flower: Four. Anther shape: Oval. Anther size: About 2 mm by 1 mm. Anther color: 12B with 200B suture lines. Pollen amount: Scarce. Pollen color: 14A. Pistils: Quantity per flower: One. Pistil length: About 1.1 cm. Style length: About 9 mm. Style color: 145C. Stigma shape: Club-shaped. Stigma color: 145A. Ovary color: 144A.

*Seed/fruit.*—Seed and fruit production has not been observed.

Disease/pest resistance: Plants of the new Sutera have not been noted to be resistant to pathogens or pests common to Sutera.

Temperature tolerance: Plants of the new Sutera have been observed to tolerate temperatures from 0 to 38° C. Plants of the new Sutera have demonstrated good tolerance to wind and rain.

It is claimed:

1. A new and distinct cultivar of Sutera plant named 'Gicomwhi-14', as illustrated and described.

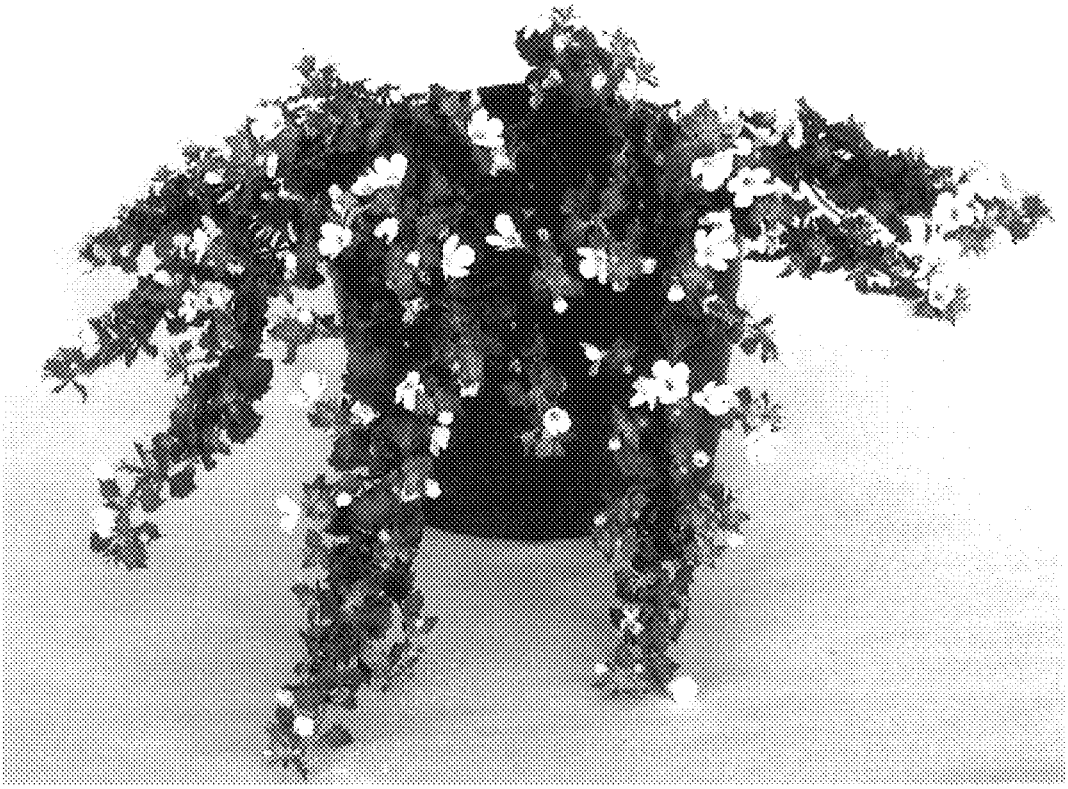
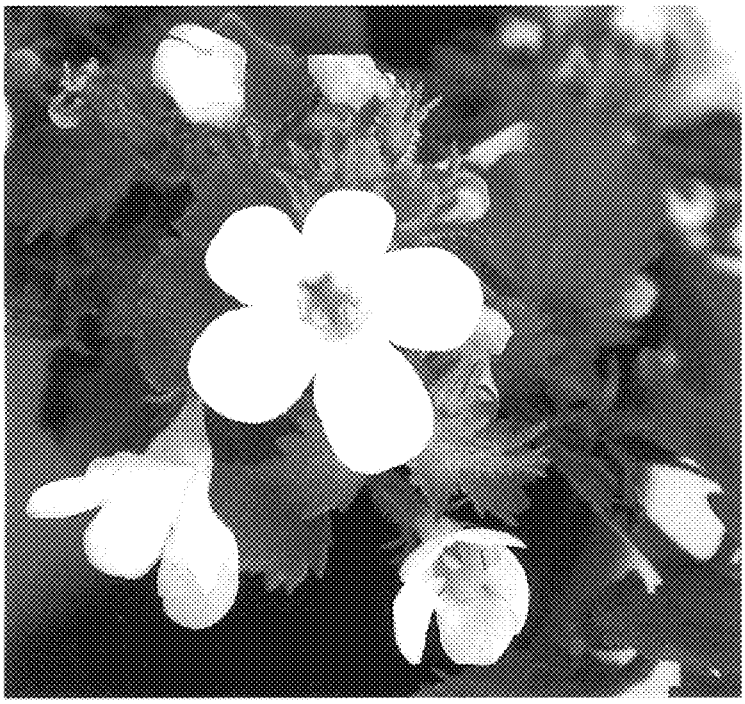

* * * * *